US012758090B2

(12) United States Patent
Li

(10) Patent No.: US 12,758,090 B2
(45) Date of Patent: Oct. 13, 2026

(54) SYSTEM AND METHOD FOR DETERMINING AN ORAL HEALTH CONDITION

(71) Applicant: Colgate-Palmolive Company, New York, NY (US)

(72) Inventor: Hongbing Li, Skillman, NJ (US)

(73) Assignee: Colgate-Palmolive Company, New York, NY (US)

( * ) Notice: Subject to any disclaimer, the term of this patent is extended or adjusted under 35 U.S.C. 154(b) by 227 days.

(21) Appl. No.: 18/580,532

(22) PCT Filed: Jul. 8, 2022

(86) PCT No.: PCT/US2022/036479
§ 371 (c)(1),
(2) Date: Jan. 18, 2024

(87) PCT Pub. No.: WO2023/003702
PCT Pub. Date: Jan. 26, 2023

(65) Prior Publication Data

US 2024/0324868 A1 Oct. 3, 2024

Related U.S. Application Data

(60) Provisional application No. 63/224,020, filed on Jul. 21, 2021.

(51) Int. Cl.
*A61B 1/24* (2006.01)
*A61B 1/00* (2006.01)
(Continued)

(52) U.S. Cl.
CPC .......... *A61B 1/24* (2013.01); *A61B 1/000096* (2022.02); *A61B 1/00045* (2013.01);
(Continued)

(58) Field of Classification Search
CPC . A61B 1/24; A61B 1/000096; A61B 1/00045; A61B 1/05; A61B 1/0676;
(Continued)

(56) References Cited

U.S. PATENT DOCUMENTS

| | | | |
|---|---|---|---|
| 5,742,700 A | 4/1998 | Yoon et al. |
| 9,113,781 B2 | 8/2015 | Wels et al. |

(Continued)

FOREIGN PATENT DOCUMENTS

| | | |
|---|---|---|
| CN | 106875386 | 6/2017 |
| CN | 111126574 | 5/2020 |

(Continued)

OTHER PUBLICATIONS

Machine translation for WO 2019/150515, IDS (Year: 2019).*
(Continued)

*Primary Examiner* — Qian Yang

(57) ABSTRACT

A system for determining an oral care condition within an oral cavity. The system may include an intraoral device which has a light source for emitting light within the oral cavity and a camera to capture an image of at least one tooth and adjacent gums. The system may include one or more processors configured to: receive the image of the at least one tooth and adjacent gums, differentiate the at least one tooth and the adjacent gums adjacent as a tooth segment and a gums segment, input the gums segment into a machine learning model, and determine, via the machine learning model, the oral care condition based on the gums segment input into the machine learning model.

20 Claims, 6 Drawing Sheets

(51) Int. Cl.

| | |
|---|---|
| ***A61B 1/05*** | (2006.01) |
| ***A61B 1/06*** | (2006.01) |
| ***G16H 50/20*** | (2018.01) |

(52) U.S. Cl.

CPC .............. *A61B 1/05* (2013.01); *A61B 1/0676* (2013.01); *A61B 1/0684* (2013.01); *G16H 50/20* (2018.01)

(58) Field of Classification Search

CPC ... A61B 1/0684; A61B 5/0077; A61B 5/7264; A61B 5/0088; G16H 50/20

See application file for complete search history.

(56) References Cited

U.S. PATENT DOCUMENTS

| | | | |
|---|---|---|---|
| 9,626,462 | B2 | 4/2017 | Somasundaram et al. |
| 10,405,796 | B2 | 9/2019 | Ribnick et al. |
| 10,679,325 | B2 | 6/2020 | Park et al. |
| 10,685,259 | B2 | 6/2020 | Salah et al. |
| 10,792,127 | B2 | 10/2020 | Kopelman et al. |
| 10,867,385 | B2 | 12/2020 | Hibbard et al. |
| 10,898,077 | B2 | 1/2021 | Kopelman et al. |
| 10,916,008 | B2 | 2/2021 | Somasundaram et al. |
| 2019/0150825 | A1 | 5/2019 | Kambara |
| 2019/0313963 | A1 | 10/2019 | Hillen |
| 2020/0202521 | A1 | 6/2020 | Joyce et al. |
| 2020/0234831 | A1 | 7/2020 | Taniguchi |
| 2020/0320685 | A1 | 10/2020 | Anssari et al. |
| 2021/0059796 | A1 | 3/2021 | Weiss et al. |
| 2021/0073998 | A1 | 3/2021 | Brown et al. |
| 2021/0217219 | A1 | 7/2021 | Zhou et al. |

FOREIGN PATENT DOCUMENTS

| | | |
|---|---|---|
| CN | 111563887 A | 8/2020 |
| IN | 202041019938 | 6/2020 |
| JP | 2019-030587 | 2/2019 |
| JP | 2020-179173 | 11/2020 |
| WO | 2015/069704 | 5/2015 |
| WO | 2016/148297 | 9/2016 |
| WO | 2019/150515 | 8/2019 |
| WO | 2020/012476 | 1/2020 |
| WO | 2020/048960 | 3/2020 |
| WO | 2020/053042 | 3/2020 |
| WO | 2021/044671 | 3/2021 |
| WO | 2023/003702 | 1/2023 |

OTHER PUBLICATIONS

Machine translation for JP 2020-179173, IDS (Year: 2020).*

Alalharith et al., 2020, "A Deep Learning-Based Approach for the Detection of Early Signs of Gingivitis in Orthodontic Patients Using Faster Region-Based Convolutional Neural Networks", international journal of Environmental Research and Public Health, 17, 8447: 1-10.

You et al., 2020, "Deep learning-based dental plaque detection on primary teeth: a comparison with clinical assessments", BMC Oral Health, 20:141.

International Search Report and the Written Opinion of the International Searching Authority issued in International Application PCT/US2022/036479 mailed Oct. 21, 2022.

Li et al., "A Deep Learning Approach to Automatic Gingivitis Screening based Onclassification and Localization in RGB Photos", Research Square: 1-13.

Liang et al., 2020, "OralCam: Enabling Self-Examination and Awareness of Oral Health Using a Smartphone Camera".

Rana et al., 2017, "Automated Segmentation of Gingival Diseases from Oral Images", IEEE: 144-147.

Yauney et al., 2018, "Automated Process Incorporating Machine Learning Segmentation and Correlation of Oral Diseases with Systemic Health", Journal of Biomedical and Health Informatics, 1-8.

Hegazy et al, 2019, "U-Net Based Metal Segmentation on Projection Domain for Metal Artifact Reduction in Dental CT", Biomedical Engineering Letters, vol. 9:375-385.

Phen-Lan Lin et al: "An automatic lesion detection method for dental xray images by segmentation using variational level set", Machine Learning and Cybernetics (ICML), 2012 International Conference On IEEE, Jul. 15, 2012 (Jul. 15, 2012), pp. 1821-1825, XP032270704, DOI: 10.1109/ICMLC2012.6359652 ISBN: 9781467314848.

Stillittano S. et al: "Inner Lip 1-15 Segmentation By Combining Active Contours and Parametric Models", Proceedings of the Third International Conference On Computer Vision Theory and Applications; Funchal, Madeira, Portugal; Jan. 22-25, 2008. Insticc Press, A61B Setúbal, G06T vol. 1, Jan. 22, 2008 (Jan. 22, 2008), pp. 297-304, XP002625885, ISBN: 9789898111210.

* cited by examiner

Gum Detection/ Filtering

Extract Gum Image

SYSTEM AND METHOD FOR DETERMINING AN ORAL HEALTH CONDITION

CROSS-REFERENCE TO RELATED APPLICATIONS

The present application claims priority to U.S. Provisional Patent Application Ser. No. 63/224,020, filed Jul. 21, 2021, the entirety of which is incorporated herein by reference.

BACKGROUND

Technology for promoting a user's health is known. In particular, connected health and consumer level diagnostic devices have been used among consumers to improve their long-term health care. For example, biometric devices may be used to ensure users are walking around and moving enough to prevent long-term muscular-skeletal problems and other health conditions.

Comprehensive consumer level biometric and diagnostic devices for oral hygiene, however, are not commonly known or available. Consumer level oral diagnostic devices have been introduced, but these devices are often lacking in functionality for improving oral health, such as for gingivitis detection and health product recommendations. Further, none of the current devices effectively utilize a consumer-grade camera and machine learning techniques for performing such diagnoses. Thus, an intraoral device using a consumer grade camera for determining oral cavity conditions, such as gingivitis, is desired.

BRIEF SUMMARY

The present disclosure may be directed, in one aspect, to a method, device, and/or system for determining a gingivitis condition within an oral cavity. For example, a system may include an intraoral device and/or one or more processors. The intraoral device may include a light source configured to emit light within the oral cavity a camera configured to capture an image of one or more objects within the oral cavity. The one or more processors may be configured to receive the image of the one or more objects within the oral cavity, wherein the one or more objects comprising at least one tooth and gums surrounding the at least one tooth; differentiate the at least tooth and the gums surrounding the at least one tooth as a tooth segment and a gums segment; input the gums segment into a machine learning model; and determine, via the machine learning model, the gingivitis condition based on the gums segment input into the machine learning model. The camera may be a consumer grade camera. The machine learning model may determine the gingivitis condition via a deep learning technique.

BRIEF DESCRIPTION OF THE DRAWINGS

The present disclosure will become more fully understood from the detailed description and the accompanying drawings, wherein.

DETAILED DESCRIPTION

Figure 1:
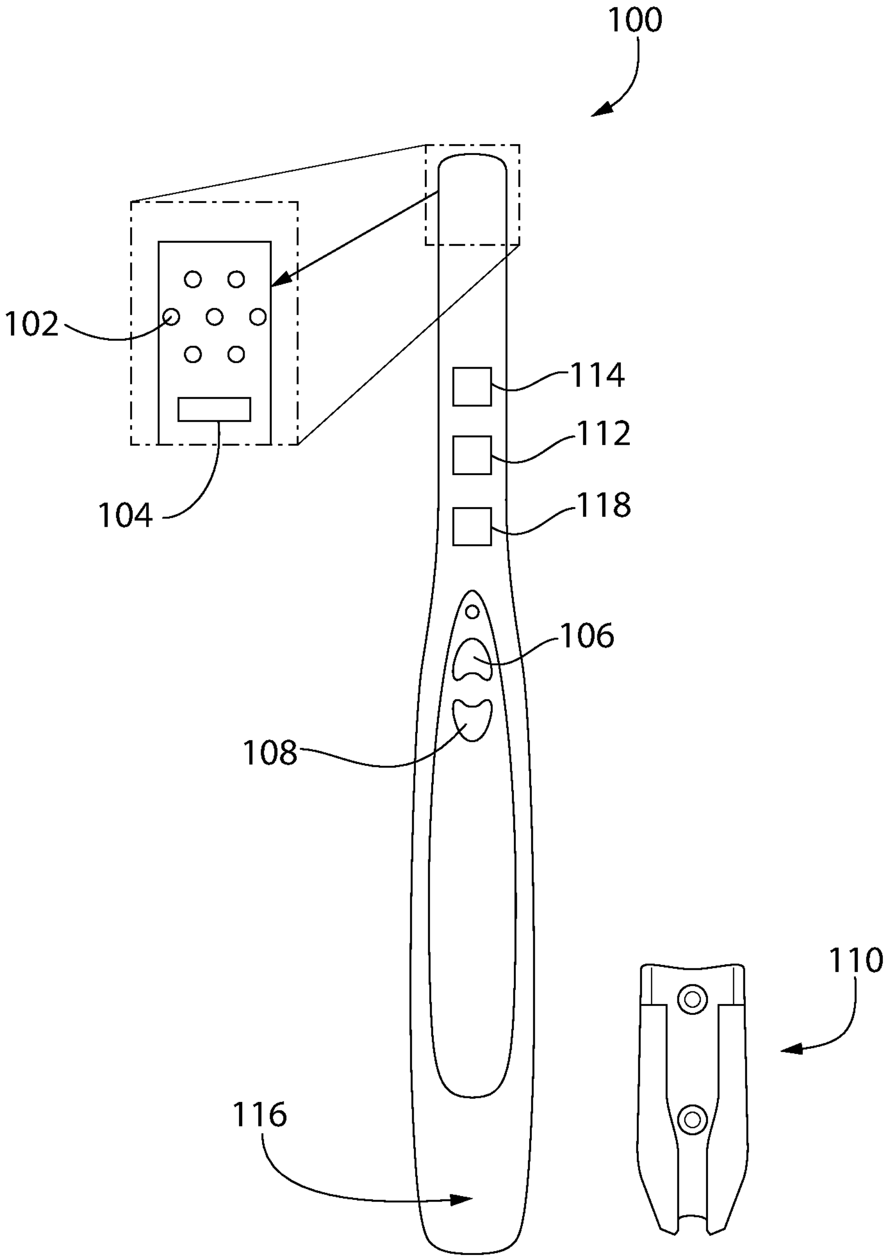
FIG. 1 is a front perspective view of an example intraoral insert device, as described herein.

The following description of the preferred embodiment(s) is merely exemplary in nature and is in no way intended to limit the invention or inventions. The description of illustrative embodiments is intended to be read in connection with the accompanying drawings, which are to be considered part of the entire written description. In the description of the exemplary embodiments disclosed herein, any reference to direction or orientation is merely intended for convenience of description and is not intended in any way to limit the scope of the present inventions. Relative terms such as "lower," "upper," "horizontal," "vertical," "above," "below," "up," "down," "left," "right." "top." "bottom," "front" and "rear" as well as derivatives thereof (e.g., "horizontally," "downwardly," "upwardly," etc.) should be construed to refer to the orientation as then described or as shown in the drawing under discussion. These relative terms are for convenience of description only and do not require a particular orientation unless explicitly indicated as such.

Terms such as "attached," "affixed." "connected." "coupled," "interconnected," "secured" and other similar terms refer to a relationship wherein structures are secured or attached to one another either directly or indirectly through intervening structures, as well as both movable or rigid attachments or relationships, unless expressly described otherwise. The discussion herein describes and illustrates some possible non-limiting combinations of features that may exist alone or in other combinations of features. Furthermore, as used herein, the term "or" is to be interpreted as a logical operator that results in true whenever one or more of its operands are true. Furthermore, as used herein, the phrase "based on" is to be interpreted as meaning "based at least in part on," and therefore is not limited to an interpretation of "based entirely on."

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Features of the present inventions may be implemented in software, hardware, firmware, or combinations thereof. The computer programs described herein are not limited to any particular embodiment, and may be implemented in an operating system, application program, foreground or background processes, driver, or any combination thereof. The computer programs may be executed on a single computer or server processor or multiple computer or server processors.

Processors described herein may be any central processing unit (CPU), microprocessor, micro-controller, computational, or programmable device or circuit configured for executing computer program instructions (e.g., code). Various processors may be embodied in computer and/or server hardware of any suitable type (e.g., desktop, laptop, notebook, tablets, cellular phones, etc.) and may include all the usual ancillary components necessary to form a functional data processing device including without limitation a bus, software and data storage such as volatile and non-volatile memory, input/output devices, graphical user interfaces (GUIs), removable data storage, and wired and/or wireless communication interface devices including Wi-Fi, Bluetooth, LAN, etc.

Computer-executable instructions or programs (e.g., software or code) and data described herein may be programmed into and tangibly embodied in a non-transitory computer-readable medium that is accessible to and retrievable by a respective processor as described herein which configures and directs the processor to perform the desired functions and processes by executing the instructions encoded in the medium. A device embodying a programmable processor configured to such non-transitory computer-executable instructions or programs may be referred to as a "programmable device", or "device", and multiple programmable devices in mutual communication may be referred to as a "programmable system." It should be noted that non-transitory "computer-readable medium" as described herein may include, without limitation, any suitable volatile or non-volatile memory including random access memory (RAM) and various types thereof, read-only memory (ROM) and various types thereof, USB flash memory, and magnetic or optical data storage devices (e.g., internal/external hard disks, floppy discs, magnetic tape CD-ROM, DVD-ROM, optical disk. ZIP™ drive, Blu-ray disk, and others), which may be written to and/or read by a processor operably connected to the medium.

In certain examples, the present inventions may be embodied in the form of computer-implemented processes and apparatuses such as processor-based data processing and communication systems or computer systems for practicing those processes. The present inventions may also be embodied in the form of software or computer program code embodied in a non-transitory computer-readable storage medium, which when loaded into and executed by the data processing and communications systems or computer systems, the computer program code segments configure the processor to create specific logic circuits configured for implementing the processes.

Health and/or diagnostic devices (e.g., connected health and/or diagnostic devices) may be used by consumers concerned with their short and/or long-term health care. One or more oral diagnostic devices (e.g., consumer level oral diagnostic devices) may be described herein. These devices may provide detection of an oral care condition (e.g., gingivitis) and/or provide health/or product recommendations for improving oral health.

One or more intraoral cameras (e.g., cost-effective intraoral cameras, such as consumer grade cameras) may be coupled to oral diagnostic devices and/or may connect (e.g., wirelessly connect) to smart devices. Smart devices may include mobile phones, tablets, laptops, and the like. The intraoral cameras may allow users to capture (e.g., efficiently capture) color images and/or video of the oral cavity of the user. The images may be RGB color images or images relating to one or more other color spaces. As described herein, the oral diagnostic device may detect and/or determine conditions of the oral cavity, such as gingivitis, based on the captured images and/or video. In other examples, the images and/or video may be sent to one or more persons (such as an oral care professional) to diagnose oral tissue health and hygiene.

The oral diagnostic device may be capable of real-time detection and/or diagnosis of one or more conditions within the oral cavity. Although the disclosure focuses on gingivitis detection, such conditions may include, for example, gingivitis, plaque, teeth whiteness measurements, over brushing determinations, receding gums, periodontitis, tonsillitis, and the like. The detection and/or diagnosis of the conditions within the oral cavity may be performed via one or more artificial intelligence techniques, such as machine learning techniques. In particular, the detection and/or diagnosis of the conditions within the oral cavity may be performed via deep learning techniques, as described herein.

Diagnostic results may be provided (e.g., displayed) to a user. For example, results relating to a gingivitis diagnosis of a user may be displayed via the oral diagnostic device, one or more external devices (such as a mobile device), and the like. Other information may be displayed to the user, such as potential health implications of the diagnosis, dental visit suggestions, awards and/or recognitions for improved or excellent oral health, and/or hygiene product recommendations. Diagnostics may be saved to a smart device and/or sent (e.g., sent directly) to the user of the oral care device and/or oral care professionals allowing for monitoring of oral care health and/or hygiene progress. In examples where a smart device is used with an application (such as a smart-phone App), a virtual assistant may be activated to provide advice on improving oral health. For example, a virtual assistant may suggest brushing techniques, usage instructions of oral care products, and the like, to remedy the diagnosed oral care condition.

Referring now to the figures, FIG. 1 shows a schematic of an example oral diagnostic device 100 for determining and/or diagnosis of an oral care condition (such as gingivitis) within an oral cavity of the user. Gingivitis is a condition in which gingiva around one or more teeth become inflamed, making the gums sensitive and likely to bleed. Gingivitis can progress and lead to periodontitis, with severe inflammation and infections in the surrounding structures of the teeth. If left untreated, periodontal diseases can cause progressive bone destruction and ultimately loss of tooth. As a result, early detection and treatment of gingivitis using device 100 allows the user to treat the condition and prevent one or more unsatisfactory results, such as tooth loss.

Visual inspection and probing techniques have traditionally been used for detection and diagnosis of conditions within the oral cavity (such as gingival) in patients. Although visual inspections may be accurate, such techniques may be subjective due to differences in training, experience, and location of the oral care professionals, thereby creating errors in early diagnosis of oral cavity conditions (such as gingivitis). In contrast, artificial intelligence (e.g., machine learning and deep learning) techniques may provide an effective, automated, and accurate diagnoses of several diseases (e.g., gingivitis), as described herein.

FIG. 1 shows an example device 100 that may be used to detect one or more oral care conditions (such as gingivitis) using images acquired by one or more low cost (e.g., consumer grade) intraoral cameras. A consumer grade camera may be one or more of a non-professional camera, a non-medical camera, a camera to be used at a user's home, a camera with a lens below a quality threshold, a camera with a cost below a price threshold, etc. For example, the camera may be a 1080 P (1920×1080) camera. The camera may a 2 megapixel (MP) camera. The camera may be water proof, may include an ultra-small lens, and the like.

Figure 2:
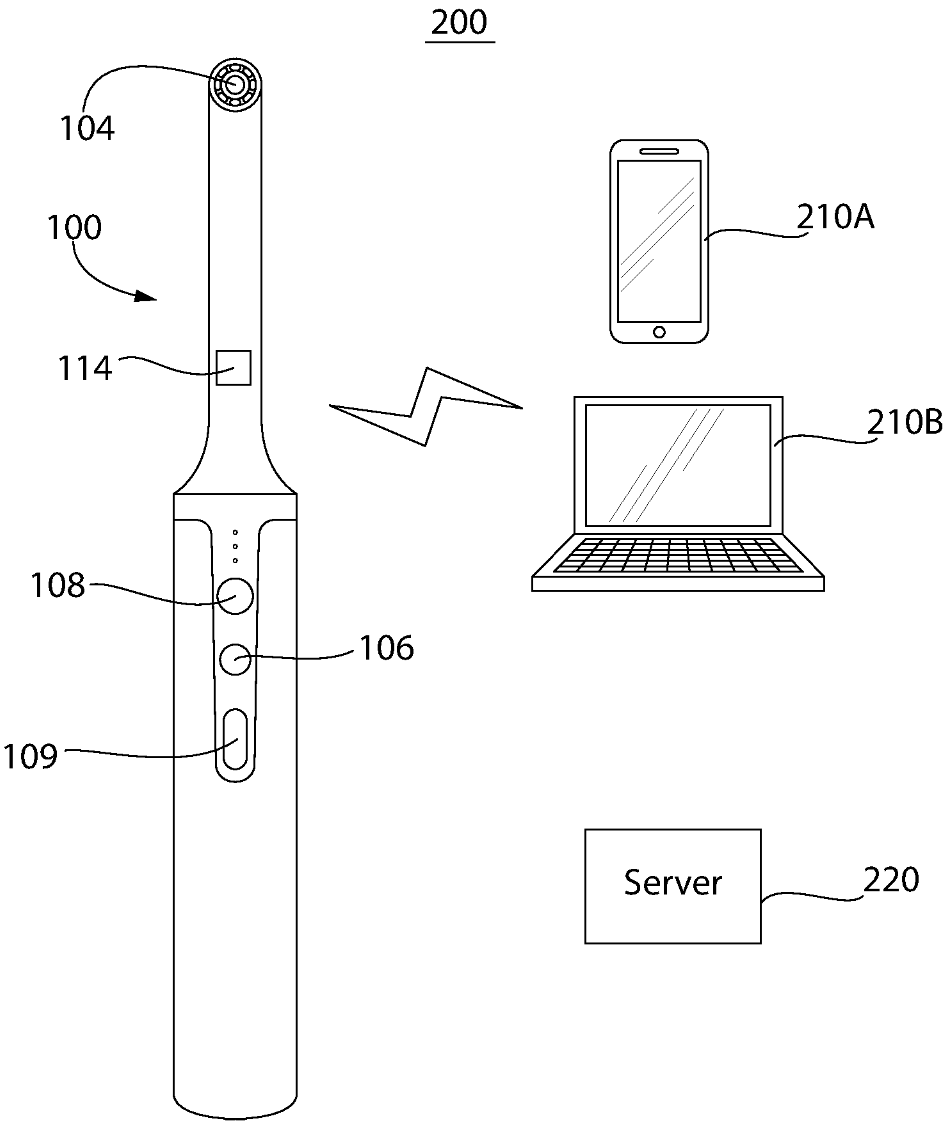
FIG. 2 is an example system including the intraoral insert device, as shown on FIG. 1.

FIG. 2 shows an example system 200 including device 100 that may be used to detect one or more oral care conditions. Using the device and/or system described herein, images of different oral cavities may be captured with one or more (e.g., different) low cost, consumer-grade, intraoral cameras. The images may be analyzed by dentists for gingivitis and used to train a machine learning model (e.g., classifier). The trained model may accept an intraoral image of gums and/or teeth and provide an automated detection of a gingivitis condition, a diagnosis of the severity of the gingivitis condition, and the like. Although the disclosure may focus on the detection and/or diagnosis of gingivitis, it should be understood that such examples are for illustration purposes only. Device 100 and system 200 may be used to determine and/or diagnose a variety of oral care conditions, as described herein.

Device 100 may contain light sources 102, which may be light emitting diodes (LEDs) (e.g., standard LEDs, organic LEDs, etc.), superluminescent diodes (SLEDs), lasers, arc lamps, a combination of the aforementioned radiation sources, other compact light sources for illuminating the oral cavity, etc. The light sources 102 may be located on one or more portions of device 100, such as on one or more portions of the hand or neck of device 100. For example, the light sources 102 may be located on a top, bottom, and/or side(s) of neck of device 100.

Device 100 may include one or more cameras, such as camera 104. Cameras 104 may be a consumer level camera that may be used to capture images of objects within the oral cavity, such as gums, teeth, etc. Camera 104 (e.g., consumer level camera) may incorporate one or more RGB cameras for imaging tissues. Camera 104 may provide qualitative information about tissue health of an oral cavity. For example, inflammation in tissue (such as gum tissue) may be captured and/or visually diagnosed as likely unhealthy. Camera 104 and light sources 102 may work in concert, such as being directed in a substantially same direction so that the camera 104 may capture an image that is well illuminated. For example, camera 104 may capture an image of at least one tooth within the oral cavity of a user and/or gums adjacent to the at least one tooth. The at least one tooth and/or gums may be well illuminated Two or more captured images may be stitched together to form a complete view of the oral cavity (e.g., the entire oral cavity). One or more single images may be provided to a machine learning model and/or one or more stitched images may be provided to a machine learning model, as described herein.

Camera 104 may be actuated via camera button 106. Button 106 may freeze an image prior to capturing the image and button 106 may be used to cause the camera to capture the image. In examples, a first touch of button 106 may be used to freeze the image within camera 104, and a second (e.g., consecutive) touch of button 106 may be used to capture the image. In examples differing pressures upon button 106 may cause the image to be frozen and/or captured by camera 104.

Device 100 may include a power button 108, which may be used to turn the device 100 on or turn the device 100 off. Although physical buttons may be used to power on/off device 100, capture an image, emit a light, etc. it should be understood that such actions may be actuated in one or more various ways, such as via a voice, a tap, received digital signals, and the like. In examples, device 100 may include a hand piece holder 110 that may include a power on/off function (e.g., automatic on/off function). Device 100 may include a magnetic sensor 116, which may be used to determine if device 100 is connected to a holder. In examples, upon the device 100 being connected to the holder, the device may transmit information relating to images captured within an oral cavity, as described herein.

Device 100 may include a processor 112 configured to perform one or more calculations and/or to cause one or more actions. For example, processor 112 may process data (e.g., image data), such as image data captured within an oral cavity. Example processors may be electronic circuits, systems, modules, subsystems, sub modules, devices and combinations thereof, such as Central Processing Units (CPU's), microprocessors, microcontrollers, processing units, control units, tangible media for recording and/or a combination thereof. Storage device 118 may be configured to store derived data from the processor 112.

FIG. 2 shows a system 200 including device 100 (FIG. 1) and one or more external devices, such as a server or mobile device. Device 100 may include a communication interface 114 that may facilitate device 100 communicating with the one or more devices. Example communication interfaces 114 may include Bluetooth, RFID, Wi-Fi, cellular based systems, and other wireless technologies.

Device 100 may be wirelessly connected to a mobile phone 210A and/or laptop 210B (collectively referred to as mobile device 210. Mobile device 210 may include one more other devices, such as a tablet, watch, etc. Device 100 may be wirelessly connected to one or more other devices, such as an external server 220 (e.g., the Internet/Cloud). In some examples device 100 may be self-contained. In examples in which device 100 is self-contained, the machine learning (e.g., deep learning) model may be being implemented directly on device 100. In other examples, pre-processing may be performed on device 100 and/or the pre-processed data may be sent to an external processor (e.g., on server 220) to perform machine learning techniques. In the self-contained example, the device 100 may be connected (e.g., wirelessly connected) to a smart user device or an external server (e.g., the Internet/Cloud) for updating the machine learning algorithms, updating a virtual assistant product and recommendation database, and/or sending data to a third party.

As described herein, machine learning may be used to diagnose and/or evaluate tissue health and oral hygiene. For example, images captured by the cameras (e.g., consumer grade intraoral cameras) may capture images within the oral cavity and present the images to a machine learning model. The machine learning model may be a deep learning model, although it should be understood that one or more other machine learning models may be used.

As known by those of skill in the art, machine learning may work with hand crafted features and relatively simple trainable classifiers. With typical machine learning, feature extraction may be time consuming for training of the model and inference. Deep learning is a part of machine learning based on artificial neural networks with representative learning. Deep learning has an inbuilt automatic multi stage feature learning process that learns rich hierarchical representations (e.g., features). With typical deep learning models, model training may be time consuming and require high computation power. Prediction can be very fast and does not necessary require high computation power. Prediction can be performed on edge, smart phones, embedded devices, etc. Deep learning may be performed on the images as described herein as it may be difficult to apply typical machine learning due to the difficulty of extracting inflammation features of tissue (e.g., gums) within an oral cavity. To apply deep learning techniques, gum detection and segmentation may be performed to remove tooth features of the image. Data augmentation may be performed, for example, on the training data so that additional features of the oral cavity may be evaluated by the deep learning model.

Figure 3:
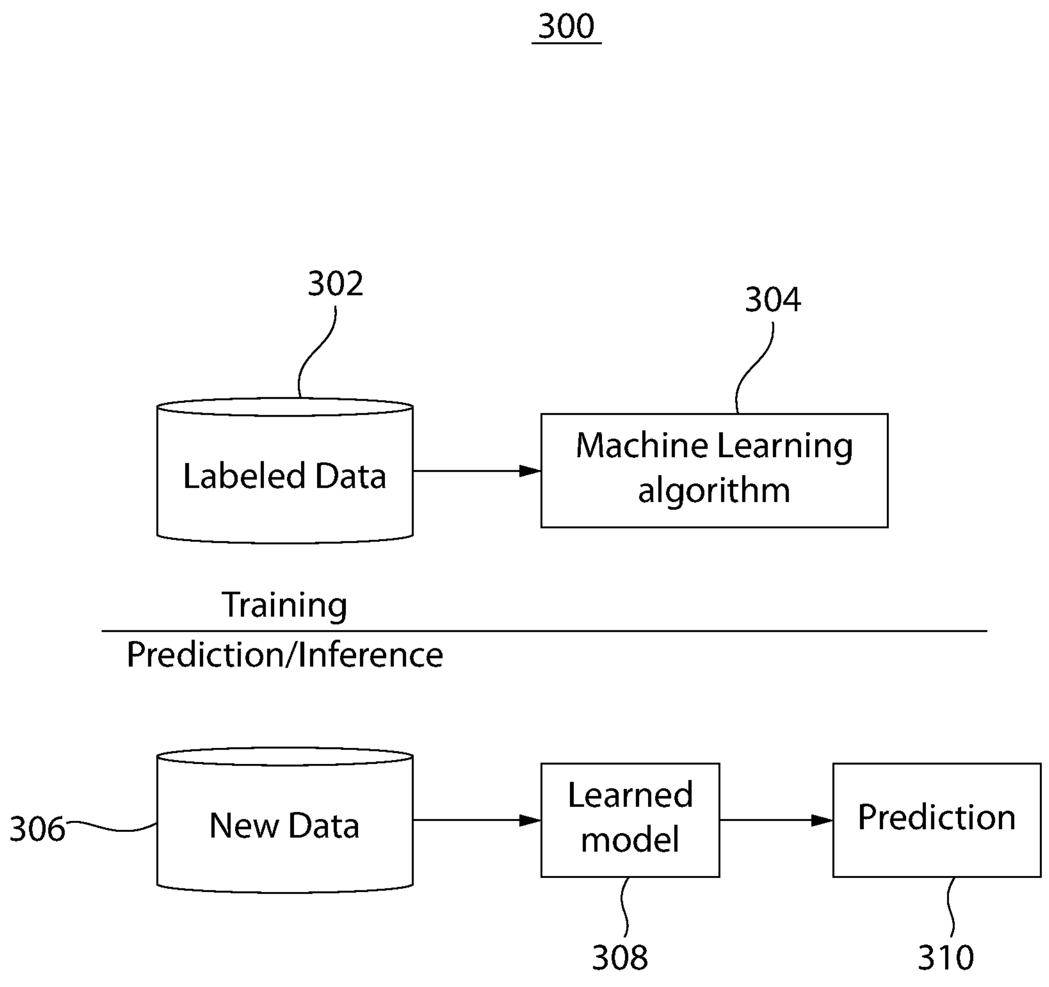
FIG. 3 shows a block diagram of using a machine learning model to determine an oral care condition, as described herein.

FIG. 3 shows an example process 300 for using machine learning (e.g. deep learning) to determine a gingivitis condition. As shown on FIG. 3, the machine learning model is trained using captured images of objects with an oral cavity. The trained model is used to predict whether a later submitted image (e.g., an image provided to the trained model) includes an oral care condition, (such as gingivitis condition), the severity of a determined oral care condition, etc. The deep-learning technique may determine (e.g., automatically determine) common features in the captured images. For example, the deep-learning technique may predict the presence or absence of an oral care condition by determining common features within a captured image that may indicate the presence, degree, or absence of an oral care condition within an oral cavity.

At 302, images may be identified and/or received that depict oral care conditions (e.g., gingivitis) and that may not depict oral care conditions. For example, images may be provided that show signs of gingivitis and images may be provided that do not show signs of gingivitis. In images depicting oral care conditions, differing degrees of the oral care condition may be shown. For example, images may be provided that shows of severs cases of gingivitis, mild cases of gingivitis, no gingivitis, and the like. Each of the images may be labeled with an indication of the severity (or absence) of gingivitis. The images and associated indication of the severity of the oral care conditions may be labeled by dental professionals, such as dentists. The images and associated indications of the presence and/or degrees of oral care conditions may be stored on a database, may be provided to the training model via wireless and/or wireless methods, and the like.

Objects within the images of the oral cavities may be segmented. For example, the oral cavities within the images may be segmented into a tooth portion and a tissue (e.g., gums) portion. The images being segmented may assist in the training of the deep learning model, as the training will be based on relevant portions of the oral cavity. For example, gingivitis detection is based on gum conditions, and not based on conditions of teeth within an oral cavity. To obtain optimal image training (e.g., classification) results, gum regions and teeth regions may be segmented. The gum regions (e.g., only the gum regions) may be presented to the model so that tooth features do not impact the trained image classifier.

For gum detection and segmentation, the image may be converted from the RGB color space to the YCrCb color space. The image may be converted from the RGB color space to the YCrCb color space as many (e.g., most) gum regions may have a Min-Max YCrCb color range. For example, many gum regions may have an YCrCb color range from (0, 138, 77) to (255, 173, 127). It should be understood, however, that such ranges are non-limiting and are for illustration purposes only. The YCrCb values may vary depending on the intraoral cameras used. Because gum regions may have outliers, such as light reflection, a post outlier removal and/or region joint operations may be used to obtain a gum region (e.g., an entire gum region). The post outlier removal may be used in addition, or alternatively to, using color ranges to perform gum image thresholding.

At 304, the images depicting oral care conditions and the associated indication of the oral care condition may be provided to a model (e.g., deep learning model) for training. The images (e.g., data) provided to the model for training may be augmented so that additional data may be provided to the training model. For example, images (e.g., original images) may be provided to the training model, and the images may be flipped (e.g., horizontally or vertically flipped) to provide additional image data to the training model. In other examples, the image may be cropped (e.g., randomly cropped, such as by cropping the image 10% or 20%) to provide additional image data to the training model. Such augmentation techniques are intended as examples only. One or more other techniques for increasing the images/data may be used. Increasing the images (e.g., image data) may increase the accuracy of the oral care condition predictions, as the training data may have additional data for the model to process and learn from. The model (e.g., machine learning model) may be housed on the device 100 and/or on one or more other devices, such as an external server, a mobile device, and the like.

The images provided to the training model may be segmented and/or un-segmented. For example, segmented gum portions may be provided to the training model. In the training phase, the model may be trained to identify common features of data in one or more data sets (e.g., classified data sets). For example, the model may be trained to identify common features of the images showing the presence or absence of gingivitis, the degrees of gingivitis (if present), and the like. The model may be trained by associating properties of provided images with the associated identifiers. For example, the model may be trained by associating oral care conditions (such as gingivitis), the degree of the oral care conditions, and the associated indications provided to the training model. As provided herein, the associated conditions may include indications of the oral care conditions, in which the indications are provided by one or more sources, such as a dentist and the like. Validation accuracy may be tracked during training of the model. The training of the model may end when validation accuracy and volition loss converge.

At 306, an image of an oral cavity may be presented to the trained model. The images may include an oral cavity in which an oral care condition may be present or not present. If an oral care condition, such as gingivitis, is present, the oral care condition may be exhibited in degrees (e.g., severe, mild, etc.). The image may be segmented or unsegmented. For example, the image may include the teeth and gums, or the image may contain only the gums. The quality of the image may be determined before the model determines an oral care condition of the oral cavity. For example, the focus of the image may be determined via the Tenengrad technique. The Tenengrad technique may convolves an image with Sobel operators and sum the square of the magnitudes greater than a threshold. Equation 1.0 below shows the Tenengrad technique:

$$F_{TEN} = \sum_{i,j} [g(i, j) \otimes S]^2 + [g(i, j) \otimes S']^2, \quad \text{Equation 1.0}$$

where S and S' are Sobel's kernel and its corresponding transpose, respectively:

$$S = \begin{bmatrix} 1 & 0 & -1 \\ 2 & 0 & -2 \\ 1 & 0 & -1 \end{bmatrix}$$

At 308, the image may be presented to the model (e.g., the trained or learned model). The model may reside on device 100 or may reside external to device 100. At 310, the model may determine (e.g., predict) an oral care condition of the oral cavity within the presented image. The oral care condition may include the presence of an oral care condition (e.g., gingivitis), the absence of the oral care condition (e.g.

the oral care is healthy), a location of the oral care condition, the degree of the oral care condition present within the oral cavity, and the like. For example, the predicted oral care condition may include a prediction of whether the gum in the image is inflamed, where the condition (e.g., inflammation) may be found, remediation possibilities for the oral care conditions, etc. The model may determine that the oral cavity within the image includes a mild case of gingivitis at teeth numbered 29 and 30. The model may indicate that the user of device should treat the oral care condition with, for example, a special tooth paste. In another example the model may predict a severe case of gingivitis and indicate that the user of the device should immediately be seen by a dentist to treat the gingivitis.

FIGS. 4A-4D and 5A-5D show example segmentations of oral cavities depicted within images. Images of oral cavities used for training the model (e.g., deep learning model) may be segmented, and images of oral cavities in which oral care conditions may be predicted via the trained model (e.g., deep learning model) may be segmented. One or more objects within the oral cavity shown on the images may be segmented. The segmented images may be provided to the machine learning (e.g., deep learning) model.

FIGS. 4A-4D show an image segmentation of an oral cavity in which the gums depicted are unaffected by gingivitis or the gingivitis is mild. FIGS. 5A-5D show an image segmentation of an oral cavity in which the gums depicted are severely affected by gingivitis.

Figure 4A:
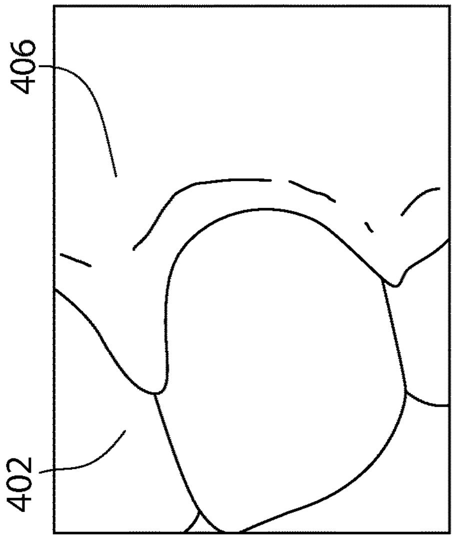
FIGS. 4A-4D show an example detection and segmentation of gums within an image, as described herein.

FIG. 4A shows an image of the oral cavity. As shown on FIG. 4A, the image may include one or more teeth 402 and gums 406. Image processing may be performed on the image, such as determining whether the quality of the image is approved for being input into the deep learning model for prediction of an oral care condition. For example, whether the focus of the image is above a predetermined threshold. In addition, or alternatively, image processing may be performed that may include zooming into one or more portions of the oral cavity, such as one or more teeth, one or more portions of gums, etc. Pre-processing may be performed that may result in zooming into portions of the gum indicating a presence of gingivitis, such as if gum portions are different colors than other portions of the gums.

Figure 4B:
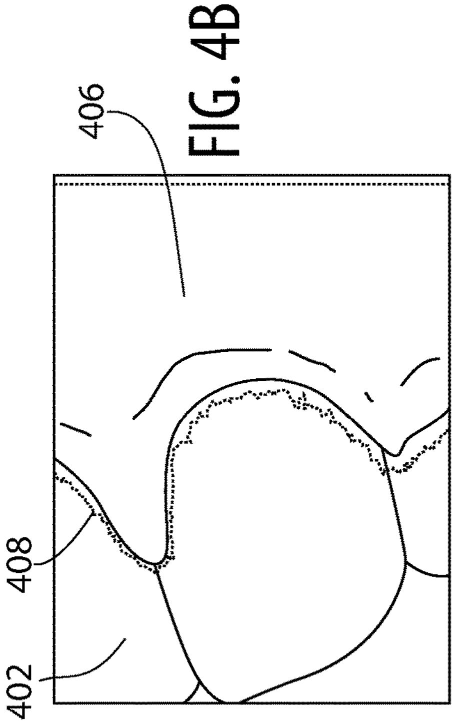

As shown on FIG. 4B, segmentation of the image may begin to be performed. Segmentation may be performed by distinguishing a tooth area and a gum area. The tooth and gum areas may be distinguished in one or more ways, such as by comparing areas against typical colors, typical shapes, and the like. For example, a tooth segmentation may be defined according to a white, off-white, or yellow color and/or a curved or jagged shape. A gum portion may be defined according to a pink color and/or a bulbous shape. A segmentation line 408 may define the tooth 402 and gums 406 portion.

Figure 4C:
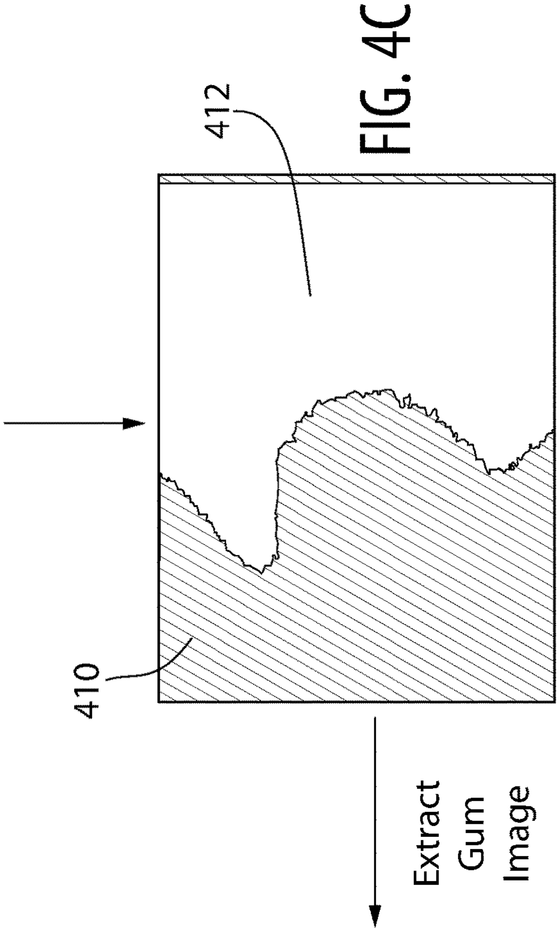
Figure 4D:
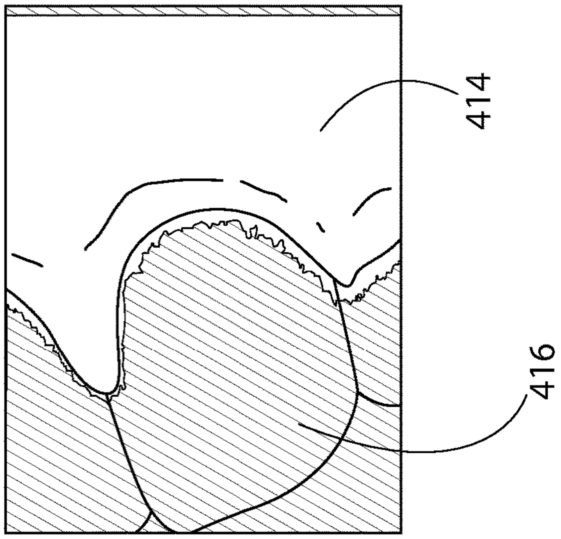

FIG. 4C shows the tooth and/or gum portion being segmented within the image. Although FIG. 4C shows tooth and gum portions remaining after segmentation (e.g., outlines of the portions remaining), it should be understood that one or both portions may remain after segmentation. FIG. 4D shows the segmented gums portion 414 being extracted. The segmented gums portion may show the presence or absence of oral care conditions that may affect the gums portion, such as gingivitis. With the segmented gums portion 414 being extracted, the remaining portion 416 may be blanked out (as shown on FIG. 4D). In other examples, the remaining portion 416 may be designated with a different color, shape, text, and the like, for indicating that the remaining portion is not to be considered by the model when predicting an oral care condition based on the image shown on FIG. 4D. The segmented gums portion 414 may be provided to the machine learning model for determination of an oral care condition, as described herein.

Figures 5A, 5B, 5C, 5D:
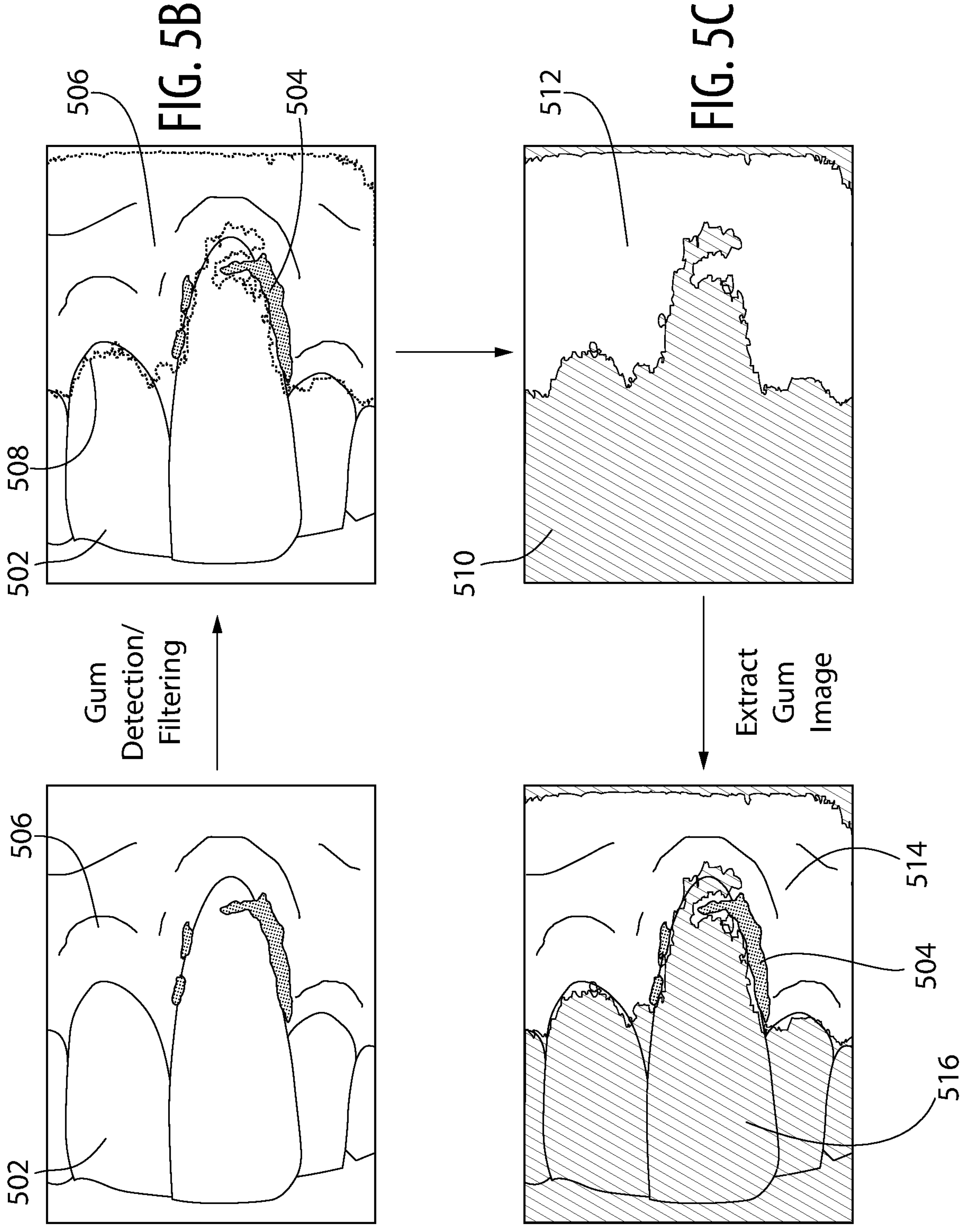
FIG. 5A-5D show another example detection and segmentation of gums within an image, as described herein.

As described herein, FIGS. 5A-5D show a segmentation of an oral cavity in which the gums depicted are severely affected by gingivitis. FIG. 5A shows an image of the oral cavity in which segmentation has not occurred. As shown on FIG. 5A, the image may include one or more teeth 502 and gums 506. FIG. 5A also shows an oral care condition affecting gums 506, such as a gingivitis condition 504. Image processing may be performed on the image, such as determining whether the quality of the image is approved for being input into the deep learning model for prediction of an oral care condition. In addition, or alternatively, image processing may be performed that may include zooming into one or more portions of the oral cavity, such as one or more teeth, one or more portions of gums. For example, preprocessing may be performed that may result in zooming into portions of the gum that indicate a presence of gingivitis (e.g., gingivitis 504).

As shown on FIG. 5B, segmentation of the image may begin to be performed. In an example, segmentation may be performed by distinguishing a tooth area and a gum area. In other examples, segmentation may be performed by distinguishing a tooth area, a gum area, and an area affected by an oral care condition (such as gingivitis) The areas may be distinguished in one or more ways, such as by comparing areas against typical colors, typical shapes, and the like. For example, a tooth segmentation may be defined according to a white, off-white, or yellow color. A gingivitis segmentation may be defined according to an off-white, gray, or yellow color that may differ from the color of the tooth segmentation. A gum portion may be defined according to a pink color. A segmentation line 508 may define the tooth 502 and gums 506 portion. In other examples a segmentation line may define the tooth, gingivitis, and gums portions.

FIG. 5C shows the tooth and/or gum portion 512 being segmented from the image. The gums portion 512 may include the portion affected by the oral care condition, as shown on FIG. 5C. Although FIG. 5C shows the tooth and/or gum portion 512 being segmented from the image, in examples the portion affected by an oral care condition may be segmented (e.g., separately segmented) from the tooth and/or gums portion. FIG. 5C shows the tooth and gums portion (e.g., outlines of the portions) remaining after segmentation. However, it should be understood that one or both portions may remain after segmentation. FIG. 5D shows the segmented gums portion 514 being extracted. The segmented gums portion may show the presence or absence of oral care conditions that may affect the gums portion, such as gingivitis. With the segmented gums portion 514 being extracted, the remaining portion 516 may be blanked out (as shown on FIG. 5D). In other examples, the remaining portion 516 may be designated with a different color, shape, text, and the like, for indicating that the remaining portion is not to be considered by the model when predicting an oral care condition based on the image shown on FIG. 5D. The segmented gum portions 514 may be provide to the model for determination of an oral care condition, as described herein.

The device (e.g., device 100) may include a smart device application that may include a virtual assistant to improve oral health, device usage, and/or case of understanding results. The virtual assistant may inform users of the meaning of results of diagnostics of the oral care condition and/or positional information of where problem areas may be located in the oral cavity. The assistant may provide brushing and/or product recommendations to improve overall health based on the individuals diagnostic. Diagnostic information may be relayed to the user through a display device (such as on a display of mobile device 210) and/or may be sent to a third party (e.g., a dentist) via an external server.

Figure 6:
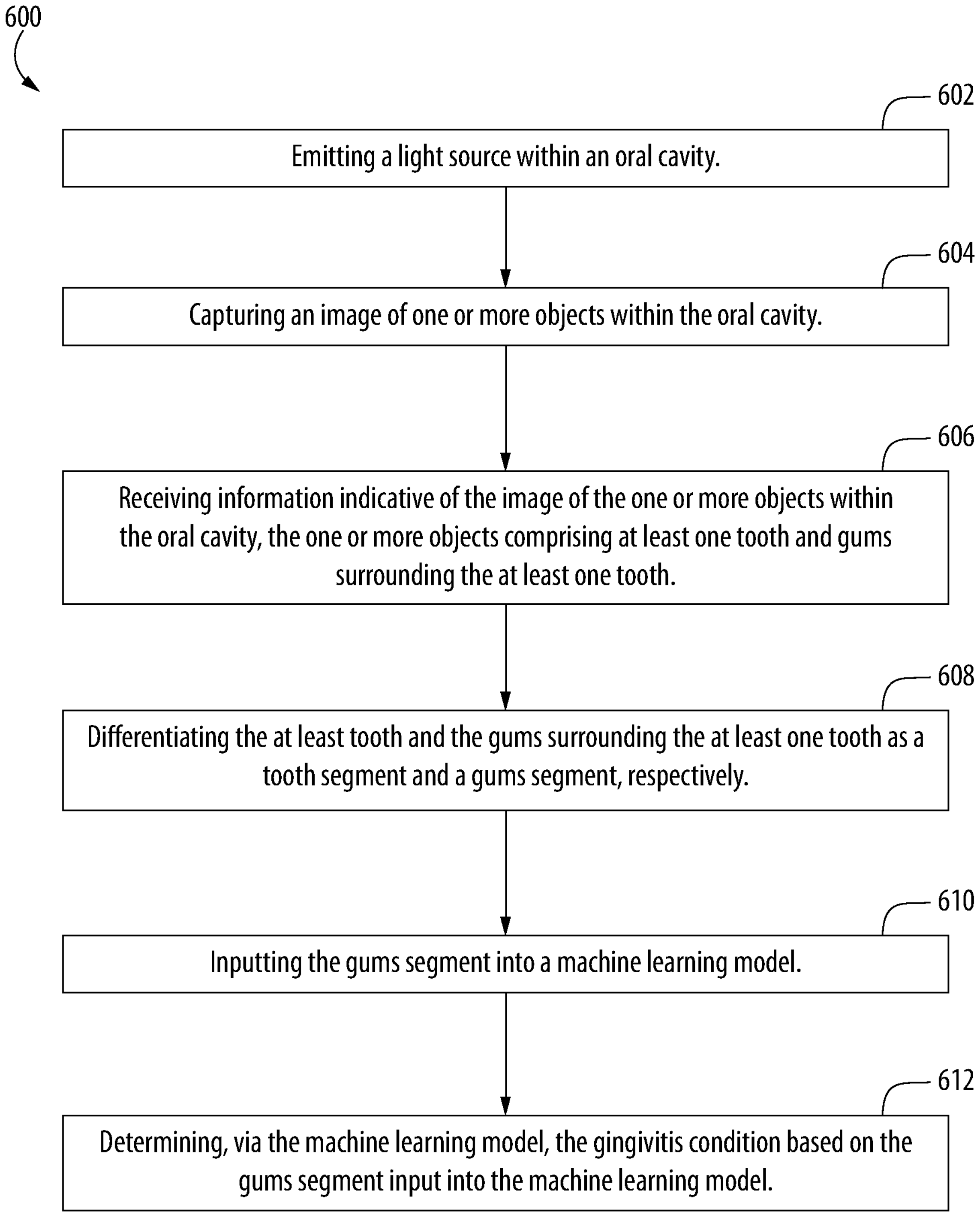
FIG. 6 describes an example process for using the intraoral insert device to determine an oral care condition (e.g., gingivitis), as described herein.

FIG. 6 describes an example process 600 for using the device 100. At 602, a light source may emit light within or about an oral cavity. The light source may be coupled to and/or housed upon a device, such as device 100. The light source may emit light upon the device being powered on in examples. In other examples, the light source may emit light upon actuation of the light button, such as light button 109 (FIG. 2). The light button may power the light source and/or perform one or more actions of the light source, such as modifying the intensity of the light emitted by the light source. The light source may emit light in one or more wavelengths, pulses, intensities, and the like. The light source may be a light emitting diode, superluminescent diode, laser, arc lamp, or the like.

At 604, an image of one or more objects (e.g., portions) within the oral cavity may be captured. The image may be captured via a consumer-grade camera. The camera may be coupled and/or housed upon a device, such as device 100. The camera may include one or more lenses, such as one or more super-wide lenses that may focus (e.g., automatically focus). The image may include the gums and/or teeth within an oral cavity.

At 606, the image of the oral cavity (e.g., data indicative of the oral cavity) may be received by one or more processors. The processor may reside on the device 100, on an external device (such as a mobile device or external server), or a combination thereto. The image may be used to train a model (e.g., deep learning model) or to determine an oral care condition, as described herein. In examples in which the image is used to train the model an associated indication of an oral care condition may be provided to the model. For example, when an image is used to train the model an indication of an oral care condition (such as gingivitis), a degree of the condition, or an absence of the condition may be provided. The associated indication may be provided by a dental professional, such as a dentist. Images (e.g., data relating to the images) may be augmented by, for example, rotating the images, cropping the images, etc. In examples in which the image is provided to the model (e.g., trained model) to determine (e.g., predict) an oral care condition, an associated indication of the oral care condition may not be provided. The images may be checked and/or filtered to determine whether the image is of a sufficient quality (e.g., proper focus) to train the model and/or to be used by the model to predict an oral care condition.

At 608, portions of the oral cavity within the image may be segmented. For example, the teeth and gums of the image may be segmented, as described herein. The teeth may be removed from the image if the teeth do not provide data relating to an oral care condition, such as a gingivitis condition. The gums may be extracted from the image so that the gums may be provided to the model for training of the model or determination of an oral care condition using the model. At 610, the segmented gums may be input into the model (e.g., deep learning model) for determination of an oral care condition. For example, the segmented gums may be input into the model (e.g., deep learning model) for determination of whether gingivitis is present on the gums, absent on the gums, and/or to what degree of severity the gingivitis is present on the gums.

At 612, the machine learning model (e.g., deep learning model) may determine an oral care condition that may be present within the oral cavity captured in the image. The machine learning model may determine the presences of the oral care condition, the severity of the condition, the absence of the condition, and the like. Information relating to the oral care condition may be provided to the user or another entity (e.g., dentist, virtual assistant, etc.). The device may display the information relating to the determined oral care condition on the device (e.g., device 100) or on an external device (such as a mobile device). The device may provide an indication of which area of the oral cavity may be affected by the oral care condition, what remediation steps may be performed to treat the oral care condition, the urgency of remediating the oral care condition, etc. Information relating to the oral care condition may be displayed, audibly provided, textually provided, and the like. The information relating to the oral care condition may be provided to the user of the device and/or to one more others, such as a dentist of the user, an online marketplace for ordering of remediation products, and the like. One or more processors may perform one or more of the action described in process 600.

While the inventions have been described with respect to specific examples including presently preferred modes of carrying out the inventions, those skilled in the art will appreciate that there are numerous variations and permutations of the above described systems and techniques. It is to be understood that other embodiments may be utilized and structural and functional modifications may be made without departing from the scope of the present inventions. Thus, the spirit and scope of the inventions should be construed broadly as set forth in the appended claims.

What is claimed is:

1. A system for determining an oral care condition within an oral cavity, the system comprising:
- an intraoral device comprising:
  - a light source configured to emit light within the oral cavity; and
  - a camera configured to capture an image of at least one tooth and gums adjacent the at least one tooth within the oral cavity; and
- one or more processors configured to:
  - receive the image of the at least one tooth and gums adjacent the at least one tooth;
  - convert the image from an RGB color space to a YCrCb color space;
  - differentiate the at least one tooth and the gums adjacent the at least one tooth as a tooth segment and a gums segment, wherein differentiating comprises obtaining the gums segment by performing gum image thresholding in the YCrCb color space based on a predetermined YCrCb color range associated with gum regions, and performing at least one of post-outlier removal or a region-joining operation;
  - input the gums segment into a machine learning model; and
  - determine, via the machine learning model, the oral care condition based on the gums segment input into the machine learning model.

2. The system according to claim 1, wherein the camera is a consumer grade camera and wherein the machine learning model determines the oral care condition via a deep learning technique.

3. The system according to claim 1, wherein the light source of the intraoral device comprises a plurality of light emitting diode (LED) lights, at least one of the LED lights surrounding the camera.

4. The system according to claim 1, wherein the one or more processors are configured to populate the machine learning model via inputting, into the machine learning model, a plurality of training gums segments obtained from training images comprising the at least one tooth and gums adjacent the at least one tooth within the oral cavity.

5. The system according to claim 1, wherein at least one processor of the one or more processors is located on a mobile device or a server.

6. The system according to claim 1, wherein the one or more processors are further configured to determine degrees of severity of the oral care condition.

7. The system according to claim 1, wherein the one or more processors are configured to:

manipulate the received image of the at least one tooth and gums adjacent the at least one tooth within the oral cavity, the manipulation of the received image comprising flipping the received image or cropping the received image;

generate a new image of the at least one tooth and gums adjacent the at least one tooth within the oral cavity based on the flipping of the received image or the cropping of the received image; and input portions of the new image into the machine learning model.

8. The system according to claim 1, wherein the intraoral device comprises:

a body portion having a button configured to cause the camera to capture the image of the at least one tooth and gums adjacent the at least one tooth within the oral cavity;

a neck portion housing the light source and the camera; and wherein the camera is located on a distal portion of the neck of the intraoral device.

9. The system according to claim 1, wherein the one or more processors are configured to cause the determined oral care condition to be displayed upon a display.

10. The system according to claim 1, wherein the oral care condition comprises at least one of gingivitis, receding gums or periodontitis.

11. A method for determining an oral care condition within an oral cavity, the method comprising:

emitting light within the oral cavity via a light source operably coupled to an intraoral device;

capturing an image of at least one tooth and gums adjacent the at least one tooth within the oral cavity via a camera operably coupled to the intraoral device;

receiving the image of the at least one tooth and gums adjacent the at least one tooth within the oral cavity;

converting the image from an RGB color space to a YCrCb color space;

differentiating the at least one tooth and the gums adjacent to the at least one tooth as a tooth segment and a gums segment, wherein differentiating comprises obtaining the gums segment by performing gum image thresholding in the YCrCb color space based at least in part on a YCrCb color range associated with gum regions;

inputting the gums segment into a machine learning model; and determining, via the machine learning model, the oral care condition based on the gums segment input into the machine learning model.

12. The method according to claim 11 wherein the camera is a consumer grade camera.

13. The method according to claim 11, further comprising populating the machine learning model via inputting into the machine learning model a plurality of training gums segments obtained from training images comprising the at least one tooth and gums adjacent the at least one tooth within the oral cavity.

14. The method according to claim 11, wherein the light source of the intraoral device comprises a plurality of light emitting diode (LED) lights, at least one of the LED lights surrounding the camera.

15. The method according to claim 11, wherein the machine learning model is located on a mobile device or a server.

16. The method according to claim 11, further comprising determining, via the machine learning model, degrees of severity of the oral care condition.

17. The method according to claim 11, further comprising:

manipulating the received image of the at least one tooth and gums adjacent the at least one tooth within the oral cavity, the manipulation of the received image comprising flipping the received image or cropping the received image;

generating a new image of the at least one tooth and gums adjacent the at least one tooth within the oral cavity based on the flipping of the received image or the cropping of the received image; and inputting portions of the new image into the machine learning model.

18. The method according to claim 11, wherein the intraoral device comprises:

a body portion having a button configured to cause the camera to capture the image of the at least one tooth and gums adjacent the at least one tooth within the oral cavity;

a neck portion housing the light source and the camera; and wherein the camera is located on a distal portion of the neck of the intraoral device.

19. The method according to claim 11, further comprising displaying the determined oral care condition upon a display.

20. The method according to claim 11, wherein the oral care condition comprises at least one of gingivitis, receding gums, or periodontitis.

* * * * *